United States Patent [19]

Mesek

[11] 4,259,387
[45] Mar. 31, 1981

[54] ABSORBENT FIBROUS STRUCTURE

[75] Inventor: Frederick K. Mesek, Tinley Park, Ill.

[73] Assignee: Johnson & Johnson Baby Products Company, New Brunswick, N.J.

[21] Appl. No.: 68,046

[22] Filed: Aug. 20, 1979

Related U.S. Application Data

[63] Continuation-in-part of Ser. No. 898,199, Apr. 20, 1978, abandoned.

[51] Int. Cl.³ .................... B32B 3/30; B32B 23/02
[52] U.S. Cl. .................... 428/167; 128/284; 128/290 P; 428/171; 428/178; 428/188; 428/218
[58] Field of Search .............. 162/117, 109, 205, 206; 428/85, 92, 158, 167, 168, 170, 171, 178, 181, 188, 296, 166, 179, , 317, 161, 163, 218; 128/287, 156, 290 P, 284, 285; 264/118, 119; 156/181, 290; 19/301, 161.1

[56] References Cited

U.S. PATENT DOCUMENTS

| 2,029,370 | 2/1936 | Heldenbrand | 428/178 |
|---|---|---|---|
| 2,959,793 | 11/1960 | Bell et al. | 428/172 |
| 3,310,454 | 3/1967 | Florio et al. | 428/171 |
| 3,938,522 | 2/1976 | Repke | 128/287 |
| 3,993,820 | 11/1976 | Repke | 428/171 |
| 4,005,236 | 11/1977 | Graebe et al. | 428/178 |
| 4,103,058 | 7/1978 | Himlicek | 428/178 |
| 4,154,883 | 5/1979 | Elias | 428/218 |

Primary Examiner—Stanley S. Silverman
Attorney, Agent, or Firm—Martha A. Michaels

[57] ABSTRACT

An absorbent fibrous structure having good stability and enhanced absorbency, flexibility and feel is provided comprising a loosely compacted cellulosic fibrous batt having a plurality of narrow, dense, compacted cellulosic fibrous lines formed by compacting the entire thickness of the batt. The fibrous areas of the batt adjacent the narrow dense lines extend over the lines, creating a fibrous region of lesser density than said batt above the lines, and a substantially fiber free region or tunnel immediately adjacent the lines.

9 Claims, 9 Drawing Figures

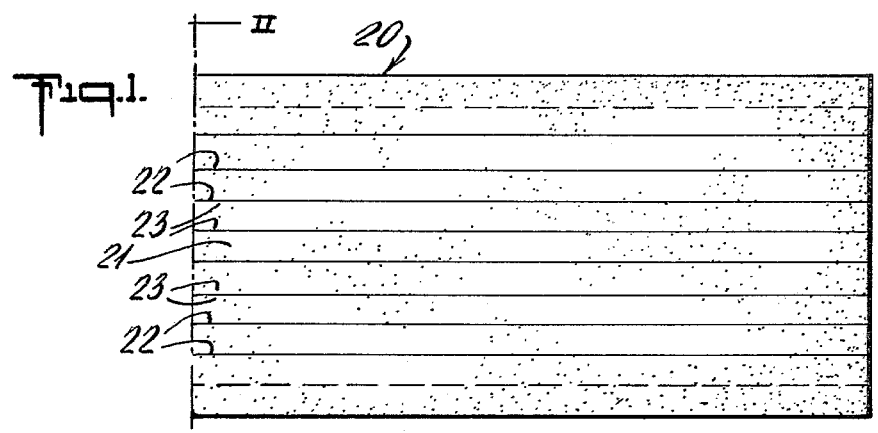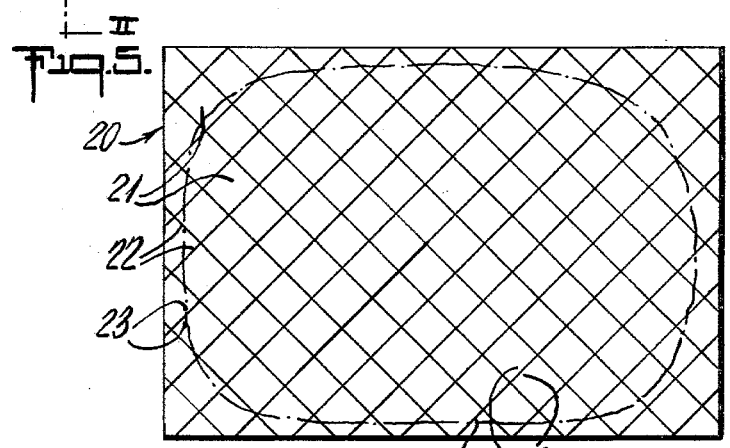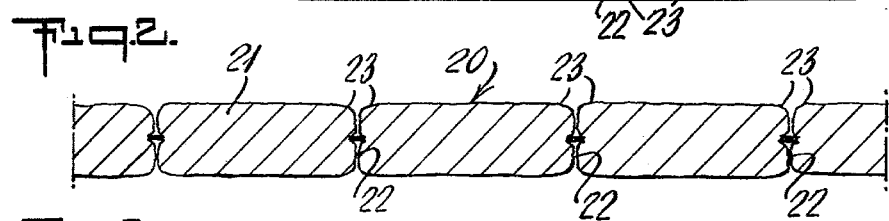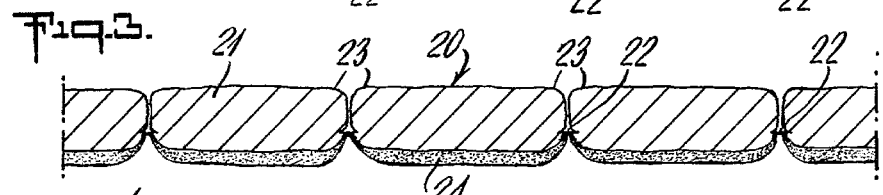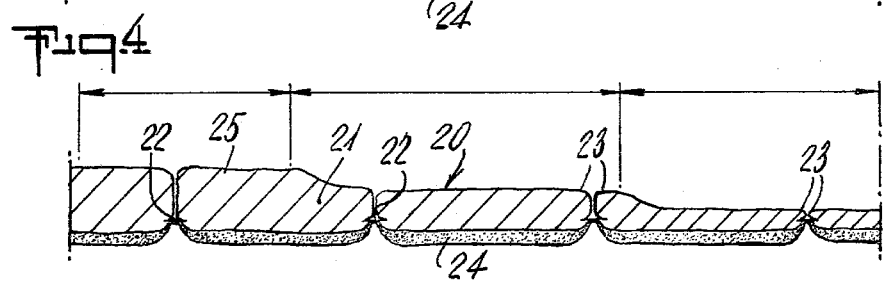

ABSORBENT FIBROUS STRUCTURE

This application is a continuation-in-part of copending application, U.S. Ser. No. 898,199, filed Apr. 20, 1978 now abandoned.

BACKGROUND OF THE INVENTION

The present invention relates generally to absorbent products and more particularly to products adapted to absorb body fluids and having paper-like densified compacted cellulosic fibrous regions, formed integrally therewith. Absorbent structures of this general type are described in U.S. Pat. Nos. 2,952,260, 2,955,641, 3,017,304, 3,060,936, 3,494,362, 3,938,522, 3,612,055 and 3,993,820. These prior art structures provide increased capillary forces to draw fluid into and throughout the densified regions, and also impart strength and stability to the absorbent structures.

The densified regions of the prior art structures, while imparting strength and stability to the absorbent structures, often impart an undesirable stiffness to the structures. Stiffness in an absorbent structure adapted for use with the human body is undesirable both in terms of feel and ability to flex or conform to a surface in use. On the other hand, the densified regions of the present invention provide good stability for the absorbent structure and leave more of the batt in a highly porous loosely compacted state. Additionally, an absorbent structure with less stiffness and greater flexibility and conformability is provided. The absorbent fibrous structures and the present invention also have improved softness and feel.

SUMMARY OF THE INVENTION

The present invention represents an improvement in stability, flexibility, liquid absorbency and feel over the heretofore known absorbent structures or panels described above, by providing a highly porous loosely compacted cellulosic fibrous batt with a plurality of spaced, relatively narrow, dense lines extending in the general plane of said batt and unitary with said batt. The dense, relatively narrow lines exhibit excellent resistance to delamination, thereby providing good stability to the absorbent structure during manufacture and when wetted during use. The lines, due to their increased density and resistance to delamination, provide sufficient stability to the absorbent structure even when very narrow, and permit the majority of the batt to remain in a loosely compacted, highly porous state that enhances the liquid holding capacity thereof. The dense lines are formed by compacting the entire thickness of the batt.

The narrow, dense lines should have a width such that the batt fibers adjacent to the dense lines extend over the lines on at least one major surface of the batt so as to substantially bridge the lines and cover at least the major portion of the exposed surface of the lines on that particular major surface of the batt along substantially the entire length of the line. These lines preferably are compacted to a density that is at least about 6 times greater than the average density of the uncompacted portions of the batt, more preferably to a density that is about 7 to about 10 times greater than the average density of the uncompacted portions of the batt. With respect to average bat thickness, the width of the narrow, dense lines preferably should not exceed about one-fifth of the average batt thickness.

Due to the relatively narrow width of the lines and their relatively high degree of compaction, the loosely compacted areas of the batt adjacent the lines "fluff over" and cover or obscure the lines with modified batt regions of lesser density than the average density of said batt, providing improved feel to the absorbent structure. Additionally, these less dense regions have a lesser tendency to attract and promote fluid flow than the relatively denser batt and the even more dense lines, and may thereby enhance the surface dryness of the absorbent structure above the wetted lines. The "fluffing over" of the dense lines by the batt fibers adjacent the dense line also create substantially fiber free areas, or tunnels, contiguous to at least one major surface of each of the lines. These tunnels may act as a fluid reservoir in a momentarily saturated area of the absorbent structure, maintaining the fluid therein until it may be wicked along the lines and absorbed into portions of the batt further removed from the saturated area. Also, in those unsaturated areas of the absorbent structure where fluid has been wicked to by the lines, the fiber free tunnels may impede the transfer of fluid from the wetted lines to the "fluffed" regions of lesser density than the batt and further to the surface of the absorbent structure. The narrowness of the lines also provides an absorbent structure that has enhanced flexibility and conformability.

In a preferred embodiment, the dense, narrow lines in an absorbent batt of density about 0.08 to about 0.1 g./cc. have a width of about 0.03 inches, and a density of about 0.77 g./cc. to 0.83 g./cc.

In use, the dense narrow lines also provide directionalized fluid flow throughout the absorbent structure. Due to the difference in density and pore size of the loosely compacted portions of the batt and the dense narrow lines, fluid preferentially flows along the narrow dense lines, and from the loosely compacted portions into and along the narrow dense lines, spreading the fluid into previously unwetted portions of the absorbent batt.

The dense narrow lines may also be used in combination with a continuous paper-like densified layer integral with the absorbent batt. In this embodiment of the invention, the dense narrow lines and densified layer cooperated to provide directionalized fluid flow into and along the dense narrow lines, bringing the fluid to and distributing the fluid throughout the densified layer, and thereby more completely utilizing the densified layer as both a fluid reservoir and a means of spreading fluid to unwetted portions of the absorbent batt.

The absorbent fibrous structures of the present invention and particularly useful as components in absorbent bandages, disposable diapers, sanitary napkins, and similar products.

BRIEF DESCRIPTION OF THE DRAWINGS

FIG. 1 is a plan view of a first embodiment of the absorbent structure of the present invention.

FIG. 2 is an enlarged fragmentary cross-section of the absorbent structure of FIG. 1 taken along lines II—II.

FIG. 3 is an enlarged fragmentary cross-section of another embodiment of the invention.

FIG. 4 is a fragmentary cross-section of another embodiment of the invention.

FIG. 5 is a plan view of another embodiment of the present invention.

DESCRIPTION OF THE PREFERRED EMBODIMENTS

Figure 6:
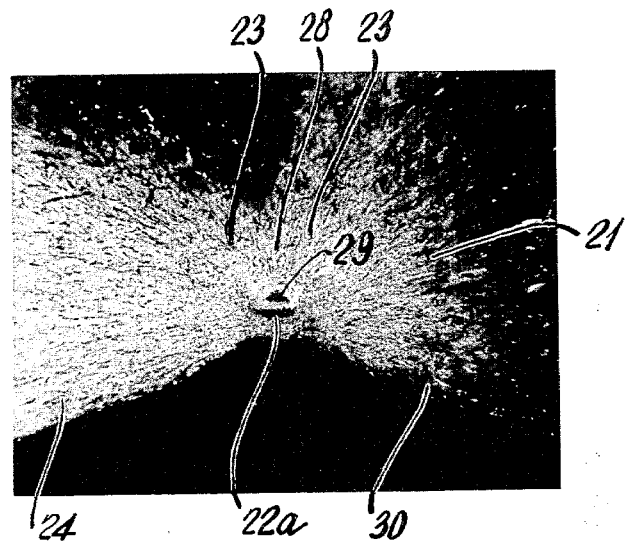
FIG. 6 is a photomicrograph of a fragmentary cross-section of a prior art structure.

A number of preferred embodiments are pictured and will be described herein, and similar elements of these embodiments will be labelled and identified with the same reference number.

Referring now to the embodiments of FIGS. 1 and 2, the absorbent structure 20 includes a loosely compacted cellulosic fibrous batt 21, and unitary therewith a plurality of narrow, spaced, paper-like, relatively dense lines 22 that extend to the transverse edges of batt 21. These narrow, dense lines are formed by compacting the entire thickness of the batt as hereinafter described. The batt 21 of absorbent structure 20 is formed of loosely compacted short cellulosic fibers such as wood pulp fibers, or cotton linters, or mixtures thereof, which are primarily held together by inter-fiber bonds requiring no added adhesive, as is known in the art. Briefly, the cellulosic fibrous batt is a low bulk density coherent web of loosely compacted fibers a major portion of which are of cellulosic origin. Preferably the batt is constituted from comminuted wood pulp fibers in the form of so-called "fluff". However, other cellulosic fibers may be used, as well as blends of cellulosic fibers with other natural fibers such as silk, wool, and the like, or with synthetic thermoplastic fibers such as polyethylene, polyester, nylon cellulose acetate, and the like.

The areas of the loosely compacted batt adjacent the narrow dense lines 23 extend over the lines providing an enhanced appearance and feel to the absorbent structure. The narrow dense lines have a substantially uniform density and are substantially free of visually observable partially delaminated fiber-free areas or "voids". These lines exhibit good strength and excellent resistance to delamination, providing good stbility to the absorbent structure.

The relatively narrow, dense lines in the absorbent structure of the present invention can be formed by passing a moist, loosely compacted fibrous batt, as described above, between a narrow-ribbed embossing roll and a back up roll. The batt should preferably have a moisture content of 5 to 10 weight percent prior to embossing.

The number, the positioning, and the spacing of the relatively narrow, dense lines can vary depending on the desired liquid transport and liquid holding characteristics of the ultimate product. Usually the number of lines per foot of width of an absorbent structure embodying the present invention is about 5 to about 25. The dense lines can be continuous or intermittent, and can be positioned substantially parallel to one another, intersecting, converging, or diverging, as desired. With respect to spacing, preferably the lines are about 15 to about 85 line widths apart, more preferably about 15 to about 60 line widths apart.

In a preferred embodiment, an absorbent structure about 10 inches wide has seven narrow, dense lines positioned in a substantially parallel relationship with respect to one another with substantially uniform spacing and having a width of about 0.015 to about 0.05 inches, more preferably of about 0.03 inches. Such lines can be formed by applying a compressive force of about 50 to 70 psi to the batt by means of a ribbed embossing roll.

In another embodiment of the invention, illustrated in fragmentary cross-section in FIG. 3, the absorbent fibrous structure also includes an integral continuous, paper-like, densified celluslosic fibrous layer 24. In this embodiment of the invention, the narrow dense lines cooperate with the densified layer to direct and increase the flow of fluid through the densified layer, bringing fluids to the unwetted portions of the absorbent batt. The densified layer and method of making the same are described in U.S. Pat. Nos. 3,612,055 and 3,993,820 which are incorporated herein by reference. It should be noted that the narrow dense lines are substantially more dense than the paper-like skin, so that liquid peferentially wicks along the narrow dense lines.

Though the narrow dense lines are illustrated in FIG. 1 as continuous and extending the full length of the absorbent structure, it should be understood that the lines may be discontinuous and need not extend to the very edge of the absorbent structure. The densified layer 24 in FIG. 3 also need not extend to the edges of the absorbent structure, thereby yielding a structure which at its edges comprises only the loosely compacted, less wickable, absorbent batt. The narrow dense lines may also be arranged in various patterns throughout the absorbent structure, one such pattern comprising a plurality of intersecting lines being illustrated in FIG. 5.

In addition, though the absorbent batt of the absorbent fibrous structure is illustrated in FIGS. 2 and 3 as having a substantially uniform thickenss of width, it should be understood that the absorbent batt may be contoured, with greater width or thickness in selected areas as in known in the art and is illustrated in FIG. 4. Further, the selected areas of greater width and/or thickness 25 of the absorbent batt may, if desired, be slightly compacted in making the absorbent fibrous structure during the embossing of the narrow dense lines or the densified layer.

Figure 7:
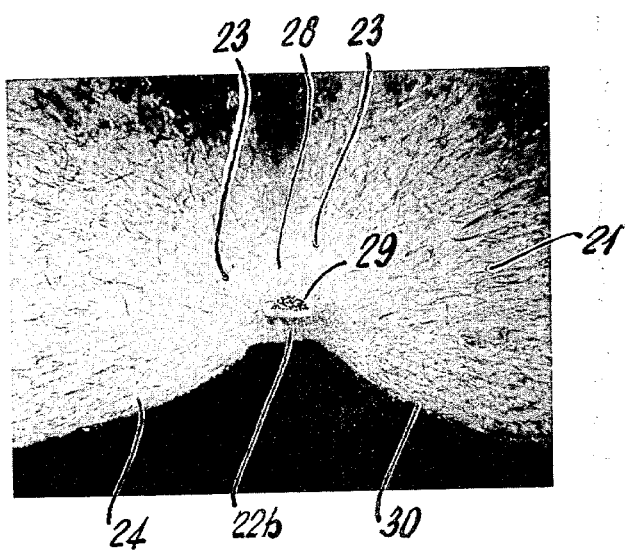
FIG. 7 is a photomicrograph of a fragmentary cross-section of another prior art structure.

FIGS. 6 and 7 illustrate in cross-section relatively wide densified regions produced in a loosely assembled cellulosic fibrous batt of a density of about 0.1 g./cc. by the method similar to that described in U.S. Pat. No. 3,993,820.

The densified region 26 in FIG. 6 was produced by applying a force of 50 psi through a five-ribbed embossing roll to produce five similar densified regions of about 0.11 inches in width. Densified region 26 has a density of about 0.20 g./cc. Densified region 27 in FIG. 7 was produced by similarly applying a force of 70 psi to produce five densified regions of about 0.11 inches in width. Densified region 27 has a density of about 0.29 g./cc.

Figure 8:
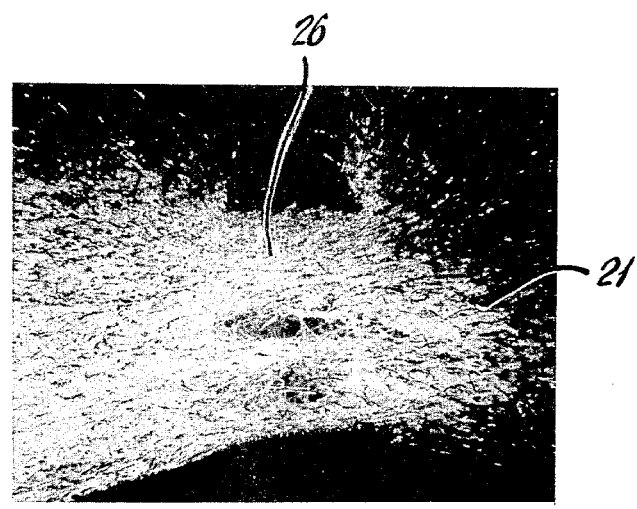
FIG. 8 is a photomicrograph of a fragmentary cross-section of one embodiment of the present invention.
Figure 9:
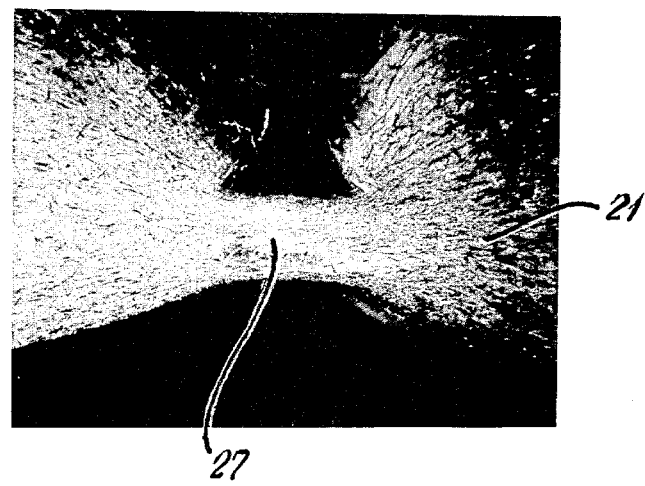
FIG. 9 is a photomicrograph of a fragmentary cross-section of another embodiment of the present invention.

FIGS. 8 and 9 illustrate partial cross-sections of two embodiments of the absorbent fibrous structure of the present invention, the cross-sections of each embodiment being taken transverse to one of the relatively narrow dense lines. The narrow dense lines were formed by a method similar to that disclosed in U.S. Pat. No. 3,993,820 but with an embossing roll provided with narrower ribs. The loosely compacted cellulosic fibrous batt 21 had an original density of about 0.1 g/cc. The narrow dense line 22a of FIG. 8 was formed by applying a pressure of 50 psi through a seven-ribbed embossing roll to produce seven similar narrow dense lines of about 0.03 inches in width and having a density of about 0.77 g./cc. The narrow dense line 22b of FIG. 9 was produced by similaryly applying a force of 70 psi to form seven similar narrow dense lines of about 0.03 inches in width and having a density of about 0.83 g./cc.

As seen in both FIGS. 8 and 9, the areas of the batt adjacent the lines 23 extend over the narrow dense lines creating a fibrous region 28 of lesser density than the average density of the batt and also creating a substantially fiber free region or tunnel 29 contiguous to one major surface of the line. Formation of a fibrous region 28 and a fiber free or tunnel 29 on major surface 30 of the batt was prevented by prior formation therein of a paper-like, densified, compacted cellulosic fibrous layer 24.

The narrow dense lines provide a preferred pathway for fluid flow, wicking fluid to unwetted portions of the batt. The fibrous regions 28 of lesser density than the batt which overlie the narrow dense lines, have a lesser tendency to wick fluids than the batt, the densified layer, and the narrow dense lines, and may promote surface dryness of the absorbent fibrous structure over the lines when they are wetted. In addition, it is thought that the substantially fiber free regions or tunnels 29 may, in a saturated region of the absorbent fibrous structure, act as a fluid reservoir, holding the fluid until it can be wicked away by the narrow dense lines. It is also thought that the regions or tunnels 29, in unsaturated regions of the absorbent fibrous structure, also promote surface dryness of the structure by their inability to transmit fluid from wetted, narrow dense lines to the fibrous regions 28 and toward the surface of the structure.

The following examples illustrate specific embodiments of the present invention.

EXAMPLE 1

Samples are cut from a highly porous loosely compacted cellulosic fibrous batt in 3"×8" sections. Each section is provided with four dense lines. In samples A–D, the dense lines are ⅛" wide. In samples E–H, the dense lines are 1/32" wide.

A test to determine the wicking properties afforded the samples by the dense lines is as follows:

The test apparatus consists of two matching clear-plastic plates measuring 5"×11". The gap between the plates is regulated with adjusting screws so as to apply the pressure required to obtain the desired density. Fibrous batt strips measuring 3"×8" (the batts generally weighing about 8 oz/yd$^2$) are placed between the plates with the bottom edge of the batt strip matching the bottom edge of the plates. The plate gap is adjusted to give whatever dry density is desired. The apparatus is then hung in a vertical position. A large Petri dish, containing 1.59% saline solution is placed on an adjustable stand and is raised to contact the bottom surface of the batt strip. The distance wicked by the liquid and the weight of the solution wicked is determined after a prescribed period of time.

The results of the tests are in Table 1 below.

TABLE 1

| Sample | Width Of Dense Line | Weight In Grams | Time In Seconds To Wick 8" | | Liquid Total Grams | Wicked Gm.Liq./ Gm.Sample | |
|---|---|---|---|---|---|---|---|
| A | ⅛" | 3.93 | 217 | | 20.1 | 5.1 | |
| B | ⅛" | 4.05 | 187 | Avg 216 | 20.6 | 5.1 | Avg 5.05 |
| C | ⅛" | 3.65 | 228 | | 18.7 | 5.1 | |
| D | ⅛" | 4.20 | 230 | | 20.7 | 4.9 | |
| E | 1/32" | 4.70 | 190 | | 25.9 | 5.5 | |
| F | 1/32" | 4.47 | 215 | Avg 208 | 23.6 | 5.3 | Avg 5.35 |
| G | 1/32" | 3.67 | 227 | | 19.9 | 5.4 | |
| H | 1/32" | 3.84 | 198 | | 20.0 | 5.2 | |

Surprisingly, it can be seen from the above that the narrow dense lines wick more liquid in approximately the same length of time than do lines four times their width. This is very significant because densified regions in fibrous batts do not hold as much liquid as non-densified regions. Thus it is desirable to densify as little of the batt as possible.

EXAMPLE 2

Similar sections to those Example 1 are made. The densified lines are then removed from the fibrous batt, and tested in the same manner as described in Example 1. The results appear in Table 2 below.

TABLE 2

| Sample | Width Of Dense Line | Weight In Grams | Time In Seconds To Wick 7" | | Liquid Total Grams | Wicked Gm.Liq./ Gm. Sample | |
|---|---|---|---|---|---|---|---|
| I | ⅛" | 0.76 | 255 | | 4.3 | 5.6 | |
| J | ⅛" | 1.15 | 187 | | 5.1 | 4.4 | |
| K | ⅛" | 0.83 | 242 | | 3.3 | 4.0 | |
| L | ⅛" | 1.25 | 210 | Avg 229 | 6.5 | 5.2 | Avg 4.71 |
| M | ⅛" | 1.76 | 277 | | 8.1 | 4.6 | |
| N | ⅛" | 2.40 | 170 | | 10.3 | 4.3 | |
| O | ⅛" | 1.30 | 275 | | 4.8 | 3.7 | |
| P | ⅛" | 0.76 | 215 | | 4.5 | 5.9 | |
| Q | 1/32" | 0.48 | 240 | | 1.9 | 4.0 | |
| R | 1/32" | 0.47 | 225 | | 2.7 | 5.7 | |
| S | 1/32" | 0.76 | 207 | | 3.7 | 4.9 | |
| T | 1/32" | 1.26 | 210 | | 7.5 | 6.0 | |
| U | 1/32" | 1.50 | 210 | Avg 240 | 9.9 | 6.6 | Avg 5.16 |
| V | 1/32" | 1.96 | 255 | | 10.2 | 5.2 | |
| W | 1/32" | 1.51 | 300 | | 6.9 | 4.5 | |
| X | 1/32" | 2.10 | 255 | | 10.2 | 4.9 | |
| Y | 1/32" | 0.49 | 260 | | 2.3 | 4.7 | |

EXAMPLE 3

Two dense lines are placed on samples made of the same batt and size as in Examples 1 and 2. The same test is used to compare the wicking of the narrow dense line with a densified line four times as wide.

The results are in Table 3 below.

TABLE 3

| SAMPLE | WIDTH OF DENSE LINE | WEIGHT IN GRAMS | TIME IN SECONDS TO WICK 7" | LIQUID WICKED Total Grams | Gm.Liq./ Gm. Sample |
|---|---|---|---|---|---|
| 1 | ⅛" | 4.10 | 200 | 22.5 | 5.5 |
| 2 | ⅛" | 3.86 | 210 | 20.0 | 5.2 |
| 3 | 1/32" | 3.95 | 210 | 22.3 | 5.6 |

TABLE 3-continued

| SAMPLE | WIDTH OF DENSE LINE | WEIGHT IN GRAMS | TIME IN SECONDS TO WICK 7" | LIQUID WICKED Total Grams | Gm.Liq./ Gm. Sample |
|---|---|---|---|---|---|
| 4 | 1/32" | 4.05 | 218 | 22.0 | 5.4 |

In each of the examples above, about the same amount of liquids wicks in about the same amount of time even when only two dense lines are used.

Due to the narrowness of the dense lines of the absorbent fibrous structure, the structure is less stiff and more flexible and conformable than comparable absorbent fibrous structures having wider less dense lines. The narrow dense lines also provide lines of increased flexibility. Because of the effective fluid transport by the narrow lines, less of the absorbent batt need be utilized to form the relatively dense regions needed to stabilize the batt, and indeed a greater number of narrow dense lines may be used to increase the stability and flexibility of the structure without substantially affecting the overall absorbency of the absorbent structure. And, the improved liquid handling capacity of the absorbent fibrous structure having narrow dense lines is achieved with enhanced panel integrity, wet strength, etc., which is surprising since those skilled in the art would expect that the absorbent panel would be weakened by application of pressure sufficient to form the narrow dense lines of the present invention.

The absorbent structures described above may be used in a wide variety of end products such as disposable diapers, sanitary napkins, bed pads, surgical dressings, and other products intended to absorb body fluids. Specifically, the absorbent fibrous structure of the present invention may be disposed a porous facing layer and a water-impervious backing sheet and adhered to the backing sheet to form an improved disposable diaper. Such a diaper construction would have good stability and enhanced absorbency, surface dryness, flexibility and feel imparted to it by the absorbent fibrous structure. In addition the diaper would have an improved appearance as the obscured narrow dense lines would not be readily visible through the water-impervious backing sheet when the absorbent panel of a diaper is an absorben structure of the type illustrated in FIG. 2.

It will be understood by those skilled in the art that variations and modifications of the specific embodiments described above may be employed without departing from the scope of the invention as defined in the appended claims.

I claim:

1. An absorbent fibrous structure having good stability and enhanced absorbency, flexibility and feel comprising a highly porous loosely compacted cellulosic fibrous batt having opposed major surfaces, and a plurality of spaced, narrow, dense, compacted cellulosic fibrous lines integral with said batt and formed by compacting the entire thickness of said batt, said narrow dense lines having good strength and excellent resistance to delamination, said lines being sufficiently narrow that the areas of the batt adjacent said narrow dense lines extend over and obscure said narrow dense lines with fibrous regions of lesser density than the average density of said batt, the surfaces of said absorbent structure being recessed inwardly at said regions of lesser density than said batt.

2. An absorbent fibrous structure having good stability and enhanced absorbency, flexibility and feel comprising a highly porous loosely compactd cellulosic fibrous batt having opposed major surfaces, and a plurality of spaced, narrow, dense, compacted cellulosic fibrous lines integral with said batt and formed by compacting the entire thickness of said batt, said narrow lines having good strength and excellent resistance to delamination, said lines being sufficiently narrow that the areas of said batt adjacent said narrow lines extend over and obscure said narrow dense lines with regions of lesser density than the average density of said batt, and defining substantially fiber free regions immediately adjacent said narrow dense lines, the surfaces of said absorbent structure being recessed inwardly at said regions of lesser density than said batt.

3. An absorbent fibrous structure as in claim 1 or claim 2, wherein the narrow dense lines are generally parallel with one another and extend to the edges of the batt.

4. An absorbent fibrous structure as in claim 1 or claim 2, wherein said dense compacted cellulosic fibrous lines each have a width of no more than about 0.03 inches.

5. An absorbent fibrous structure having good stability and enhanced absorbency, flexibility and feel comprising a highly porous loosely compacted cellulosic fibrous batt having opposed major surfaces, and a plurality of spaced, narrow, dense, compacted cellulosic fibrous lines integral with said batt and formed by compacting the entire thickness of said batt, said narrow lines having good strength and excellent resistance to delamination, said lines being sufficiently narrow that the areas of said batt adjacent said narrow lines along one major surface extend over and obscure said narrow dense lines with fibrous regions of lesser density than the average density of said batt, said absorbent fibrous structure having a paper-like densified cellulosic fibrous layer integral with said batt and extending continuously over substantially the entire area of the other major surface of said batt, the major surfaces of said absorbent structure being recessed inwardly at said narrow dense lines and said regions of lesser density than said batt.

6. An absorbent fibrous structure having good stability and enhanced absorbency, flexibility and fell comprising a highly porous loosely compacted cellulosic fibrous batt having opposed major surfaces, and a plurality of spaced, narrow, dense, compacted fibrous lines integral with said batt and formed by compacting the entire thickness of said batt, said narrow lines having good strength and excellent resistance to delamination, said lines being sufficiently narrow that the areas of said batt adjacent said narrow lines along one major surface thereof extend over and obscure said narrow dense lines with fibrous regions of lesser density than the average density of said batt, and defining substantially fiber free regions immediately adjacent said narrow dense lines, said absorbent fiber structure having paper-like densified cellulosic fibrous layer integral with said batt and extending continuously over substantially the entire area of the other major surface thereof, the surface of said absorbent structure being recessed inwardly at said narrow dense lines and said regions of lesser density than said batt.

7. An absorbent fibrous structure having good stability and enhanced absorbency, flexibility and feel which comprises a highly porous batt of loosely compacted cellulosic fibers, said batt having a predetermined average density and opposed major surfaces; a plurality of spaced lines unitary with said batt, of a density greater than said average batt density, and extending in the general plane of said batt; and portions of said batt adjacent each said line having a density less than said average batt density, substantially bridging the respective line and covering at least a major portion of the exposed surface of the respective line on at least one of said major surfaces and along substantially the entire length thereof.

8. An absorbent fibrous structure having good stability and enhanced absorbency, flexibility and feel comprising a highly porous, loosely compacted cellulosic fibrous batt having opposed major surfaces, and a plurality of spaced narrow dense compacted cellulosic fibrous lines integral with said batt and formed by compacting the entire thickness of said batt, said narrow dense lines having a width from about 0.015 to about 0.05 inch and having good strength and excellent resistance to delamination, said lines being sufficiently narrow that the areas of the batt adjacent said narrow dense lines cover at least the major portion of the exposed surface of the lines with fibrous regions of lesser density than the average density of said batt, the surfaces of said absorbent structure being recessed inwardly at said regions of lesser density than said batt.

9. An absorbent fibrous structure of claim 8 wherein the fibrous regions adjacent the narrow dense line cover at least a major portion of the exposed surface of each line along substantially the entire length of the line.

* * * * *